United States Patent [19]

Taylor et al.

[11] Patent Number: 4,678,796

[45] Date of Patent: Jul. 7, 1987

[54] 2-ALKYLIDENE DERIVATIVES OF 1,2,3,4-TETRAHYDROPYRIDINE-2,5-PYRIDINE CARBOXYLIC ACID DIALKYL ESTERS USEFUL FOR TREATMENT OF CARDIOVASCULAR DISORDERS

[75] Inventors: Michael D. Taylor, Ann Arbor; Edward W. Badger, Dexter, both of Mich.

[73] Assignee: Warner-Lambert Company, Morris Plains, N.J.

[21] Appl. No.: 903,882

[22] Filed: Sep. 3, 1986

Related U.S. Application Data

[63] Continuation of Ser. No. 677,150, Nov. 30, 1984, abandoned.

[51] Int. Cl.$^4$ .................. C07D 211/90; C07D 401/12; C07D 405/12; A61K 31/455
[52] U.S. Cl. ..................................... 514/356; 546/321; 546/263; 546/271; 546/283
[58] Field of Search ......................... 546/321; 514/356

[56] References Cited

U.S. PATENT DOCUMENTS

| | | | |
|---|---|---|---|
| 3,905,983 | 9/1975 | Bossert et al. | 546/321 |
| 4,532,248 | 7/1985 | Franckowiak et al. | 514/352 |

FOREIGN PATENT DOCUMENTS

| | | |
|---|---|---|
| 804160 | 2/1974 | Belgium . |
| 803474 | 2/1974 | Belgium . |
| 817540 | 1/1975 | Belgium . |
| 843576 | 12/1976 | Belgium . |
| 861964 | 6/1978 | Belgium . |
| 893984 | 1/1983 | Belgium . |
| 2248150 | 4/1974 | Fed. Rep. of Germany . |
| 3239273A | 4/1984 | Fed. Rep. of Germany . |

OTHER PUBLICATIONS

Loev, B. et al., *J. Med. Chem.* (1974), vol. 17, No. 9, pp. 956–965.

Meyer, H., *Calcium Antagonists and Cardiovascular Disease*, edited by L. H. Opie, Raven Press, New York (1984).

Schramm et al., "Novel Dihydropyridine, with Positive Inotropic Action", *Nature*, vol. 303, Jun. 9, 1983 (pp. 535–537).

*Primary Examiner*—Henry R. Jiles
*Assistant Examiner*—Dale A. Bjorkman
*Attorney, Agent, or Firm*—Joan Thierstein

[57] ABSTRACT

Novel 2-(2-alkoxy-2-oxoethylidene)-1,2,3,4-tetrahydro-6-methyl-4-[2-(substituted)phenyl]-3,5-pyridinedicarboxylic acid dialkyl ester derivatives having novel inotropic and hypotensive activity, processes for their manufacture, pharmaceutical compositions, and methods for using said compounds and compositions are described.

5 Claims, No Drawings

2-ALKYLIDENE DERIVATIVES OF 1,2,3,4-TETRAHYDROPYRIDINE-2,5-PYRIDINE CARBOXYLIC ACID DIALKYL ESTERS USEFUL FOR TREATMENT OF CARDIOVASCULAR DISORDERS

This is a continuation of application Ser. No. 677,150, filed Nov. 30, 1984, now abandoned.

BACKGROUND OF INVENTION

Dihydropyridine polyesters have been described in the literature as antihypertensive and antianginal agents. For example, British Pat. No. 1,389,509 describes 1,4-dihydro-pyridine-polyesters as coronary agents. Further disclosure for cardiovascular agents used as antihypertensives, vasodilators, antifibrillatory agents, and also having marked smooth muscle effect is made for 1,2,3,4-tetrahydropyridine-3,5dicarboxylic acid derivatives in West German Application No. 3,239,273-A. Additional disclosure to dihydropyridines as calcium agonists or cardiotonics is found in Belgium Pat. No. 893,984. Other dihydropyridine polyesters useful as cardiovascular agents are disclosed in West German Application No. 2,248,150, Belgian Pat. Nos. 804,160, and 803,474, Belgian Pat. No. 861,964, Belgian Pat. No. 843,576, and Belgian Pat. No. 817,540.

The present novel 2-alkylidene dihydropyridine ester derivatives have valuable calcium antagonist and cardiotonic properties and are useful for the treatment of cardiovascular disorders.

SUMMARY OF THE INVENTION

Accordingly the present invention provides a compound of the Formula I wherein $R^1$, $R^2$, and $R^3$ are independently alkyl of from one to six carbons, inclusive, optionally substituted aryl, heteroaryl, amino, alkylamino of from one to six carbons, inclusive; $R^4$ and $R^5$ are independently H, alkyl, of from one to six carbons inclusive, or alkoxycarbonyl of from one to six carbons inclusive; n is an integer of one to five, inclusive; X may be the same or different and is selected from the group consisting of H, alkyl of from one to three carbons, inclusive, $NO_2$, halogen, methoxy, amino, and alkyl amino from one to six carbons, or a pharmaceutically acceptable salt thereof. The preferred compounds of Formula I have X as trifluoromethyl.

The present invention also relates to a pharmaceutical composition comprising a nontoxic therapeutically effective amount of a compound of Formula I as defined above with a pharmaceutically acceptable carrier, and to a method of treating mammals, including man, by administering to such mammals a dosage form of a compound of the Formula I as defined above.

DETAILED DESCRIPTION

Alkyl of from one to six carbons, inclusive, in compounds of Formula I is meant to include a straight or branch chain alkyl group such as, for example, methyl, ethyl, propyl, isopropyl, butyl, pentyl, hexyl, and isomers thereof.

Halogen means fluorine, chlorine, bromine, or trifluoromethyl.

Alkoxycarbonyl of from one to six carbons, inclusive, includes a straight or branched chained alkoxy such as, for example, methoxy, ethoxy, propoxy, butoxy, pentoxy, hexoxy, and isomers thereof.

Alkylamino of from one to six carbons, inclusive, includes mono- or di-alkyl amino wherein the alkyl group of the monoamino is of from one to six carbons, inclusive, or the two alkyl groups of the dialkylamino taken together is of from one to six carbons, inclusive. Such alkyl, thus, also includes methyl, ethyl, propyl, butyl, pentyl, hexyl, or isomers thereof.

Optionally substituted aryl includes phenyl, benzyl, or a mono- or di-substituted phenyl having one or two substituents which may be the same or different and are selected from a group consisting of alkyl of from one to six carbons, inclusive, $NO_2$, halogen, methoxy, amino or alkyl amino of from one to six carbons, inclusive.

A heteroaryl means thienyl, furyl, pyryl, pyridyl, quinolyl, isoqinolyl, pyrimidyl, pyridazinyl, quinazolyl, quinoxalyl, benzothienyl, pyrazolyl, imidazolyl, oxazolyl, isoxazolyl, thiazolyl, triazolyl, pyrazinyl, oxazinyl, thiazinyl, indolizinyl, indolyl, benzofuranyl, indazolyl, benzothienyl, benzimidazolyl, benzoxazolyl, benzioxazolyl, benzthiazolyl, benztriazolyl, benzoxadiazolyl, cinnolinyl, phthalaxinyl, naphthyridinyl, or benzothiazinyl.

The compounds of Formula I are useful as salts derived from physiologically acceptable acids. The acids may be mineral acids such as hydrochloric acid, sulfuric acid, and the like, or organic acids, such as ethanesulfonic acid, benzenesulfonic acid, p-toluenesulfonic acid, and the like; giving the hydrochloride, sulfamate, ethanesulfonate, benzenesulfonate, p-toluenesulfonate, and the like, respectively.

A further and most preferred embodiment of the present invention is the compound of Formula I wherein $R^1$, $R^2$, and $R^3$ are each ethyl, $R^4$ and $R^5$ are each H and X is trifluoromethyl, that is, 2-(2-ethoxy-2-oxoethylidene)-1,2,3,4-tetrahydro-6-methyl-4-[2-(trifluoromethyl)phenyl]-3,5-pyridinecarboxylic acid diethyl ester ($I_1$).

Generally, the compounds of Formula I may be conveniently synthesized by a Hantzsch dihydropyridine synthesis as shown in Scheme I and described in *Ann.*, Vol. 215, 1, 72, (1882); *Ber.* 18, 1744 (1885). Compounds of Formula II and Formula III in each of which $R^1$, $R^2$, $R^3$, $R^4$, $R^5$, and X are as defined above for Formula I are reacted by heating at temperature, preferably in equivalent amounts, for from 16 to 240 hours, preferably from 60 to 120 hours, in a solvent such as methanol, ethanol, isopropanol, methoxyethanol, ethoxyethanol, and the like. A preferable solvent is ethanol. Also it is preferable to begin with the solvent in an anhydrous condition. The compound of Formula II is prepared from commercially available 3-oxo-pentanedioic acid diethyl ester generally as described by P. G. Baraldi, et al, *Syn.*, p. 902 (1983), and the compound of Formula III is prepared in a manner analogous to the process described in *Org. Syn. Coll. Vol.* 4, p. 408 (1963), from appropriately substituted tolualdehyde and $R^3$—OC(O)CH$_2$—C(O)CH$_3$.

The desired compound of Formula I is isolated and purified by conventional methods. Although such isolation and purification may be difficult these do not necessitate any methods not within the skill of the ordinary artisan.

The structure of the compound of Formula I is believed to be that shown, however, it is possible the structure may be that of Formula I' or a structure intermediate between I and I' such as can be depicted as Formula I".

The compounds of Formula I are found to possess novel inotropic and hypotensive activity in vitro and in vivo and as such, are useful for the treatment of congestive heart failure, coronary heart disease, myocardial ischemia, angina, and hypertension. Particularly, the most preferred compound denoted as $I_1$, above is a superior agent for the treatment of congestive heart failure. This agent, in the anesthetized dog, produces substantial increases in contractility and decreases in blood pressure, with only moderate increases in heart rate. These effects, which are similar to those observed for other calcium antagonists, are complemented by a direct stimulatory effect on the myocardium as observed in isolated atrial tissue. Although the overall result in vitro is a negative inotropic effect, the initial direct stimulation may provide additional support to a failing heart complementary to the after load reduction resulting from vasodilation.

The usefulness of the compounds of formula I of the present invention as described above is demonstrated by their effectiveness in standard pharmacological test procedures, for example, increasing cardiac contractility. At the same time low or minimal changes in heart rate and moderate reductions in blood pressure are observed. Test procedures are described in the following paragraphs.

PROTOCOLS

(A) Test for In Vitro Myocardial Inotropic Activity in Isolated Guinea Pig Atria Adult male guinea pigs weighing 300–400 g are reserpinized (2000 units i.p.) and, after ten minutes, are killed by cervical dislocation. The hearts are quickly removed and placed in a physiological salt solution (PSS) containing: 118 mM NaCl, 4.8 mM KCl, 2.4 mM $CaCl$, 1.2 mM $MgSO_4$, 1.0 mM $NaH_2PO_4$, 11.1 mM dextrose, and 27.2 mM $NaHCO_3$, maintained at pH 7.4 and 30° C. After removing all superficial blood, the hearts are perfused via the aorta to remove any blood from the coronary arteries. After five to ten minutes of perfusion, the left atria are dissected and mounted vertically in a 50 ml, water-jacketed bather containing PSS at 30° C. and continuously oxygenated with 95% $O_2$/5% $CO_2$. The left atria are electrically stimulated at 1.5 Hz. The tissues are equilibrated for 30 minutes and washed with fresh PSS. The stimulation voltage is adjusted to 20% above the threshold and tension adjusted to Lmax (the muscle length at which tension development is maximal). The tissues are then equilibrated for an additional 30 minutes, after which the compounds to be examined are added to the tissue bather. The compounds are initially dissolved in DMSO and dilutions made with normal saline, such that the final concentration of DMSO does not exceed 0.5%. The compounds are added in full or half-log concentration increments, usually over a concentration range of $1 \times 10^{-8}$ to $1 \times 10^{-4}$ M. The muscles are generally allowed to assume a new steady-state contractile response before each subsequent addition of drug.

Using this procedure compound $I_1$, exhibited a positive inotropic effect, increasing contractility by 9 to 28% over a concentration range of $1 \times 10^{-8}$ to $1 \times 10^{-5}$ M. In contrast, the calcium antagonist 1,4-dihydro-2,6-dimethyl-4-[2-(trifluoromethyl)phenyl]-3,5-pyridinedicarboxylic acid, diethyl ester produced an immediate and marked negative inotropic effect, decreasing contractility by 0.0 to 83% over the same range of concentration.

(B) Test for In Vivo Myocardial Inotropic Activity in the Anesthetized Dog

This screen consists of determining the effects of increasing intravenous doses of compound on myocardial contractility (dp/dt max of left ventricular blood pressure), heart rate, and aortic blood pressure of the pentobarbital-anesthetized dog.

METHODS

Adult mongrel dogs of either sex are anesthetized with pentobarbital, 35 mg/kg, IV, and are subsequently maintained under anesthesia with a continuous infusion of pentobarbital, 3.5 mg/kg/hr. The trachea is intubated but the animals are permitted to breathe spontaneously. A cannula is inserted into the femoral vein for administering test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of the left ventricular blood pressure (dp/dt), obtained with a differentiator amplifier coupled to the corresponding pressure amplifier, are also recorded. A period of at least 30 minutes is utilized to obtain control data prior to administration of test compound.

The compounds are dissolved in dimethylacetamide. Each dose of the test compound is administered in a volume of 0.5 ml over a period of one minute. Appropriate vehicle controls are administered when needed.

Specifically, the most preferred compound; denoted as Formula $I_1$ above, at a doe of 1 mg/kg IV produced an increase in dp/dt of $108 \pm 25\%$, in heart rate of $12.3 \pm 4.7\%$, and a decrease in a blood pressure of $26.5 \pm 2.7\%$. These results are tabulated below.

| | EFFECT OF THE COMPOUND OF FORMULA $I_1$ ON CARDIOVASCULAR FUNCTION IN ANESTHETIZED DOGS | | | | | |
|---|---|---|---|---|---|---|
| | | | | | | After b-blockade |
| | % Change from Control mg/kg | | | | | |
| Control | 0.01 | 0.03 | 0.1 | 0.31 | 1.0 | 1.0 mg/kg |
| Heart Rate (BPM) 146 ± 16 | 2.0 ± 0.9 | 3.6 ± 0.8 | 7.6 ± 1.9 | 8.0 ± 2.8 | 12.3 ± 4.7 | 0.5 ± 0.9 |
| (dp/dt - mmHg/sec) 2482 ± 294 | 11.8 ± 1.5 | 14.2 ± 2.6 | 26.0 ± 5.8 | 57.0 ± 11.3 | 108 ± 25 | 8.3 ± 3.6 |
| Diastolic bp (mmHg) 116 ± 5 | 0.4 ± 0.5 | −1.4 ± 2.0 | −4.2 ± 1.9 | −15.2 ± 2.4 | −26.5 ± 2.7 | −10.0 ± 3.5 |
| N | 5 | 5 | 5 | 5 | 4 | 4 |

The present invention includes a method for treating mammals, including humans, suffering from the diseases noted above by administering to such mammals a corresponding pharmaceutical composition containing a compound of the Formula I as defined above in appropriate unit dosage form. A physician or veterinarian of ordinary skill readily determines a subject exhibiting symptoms of the diseases. The routes of administration and the dosage forms therefor are from among those conventional to the pharmaceutical art. Regardless of the route of administration selected the invention provides a compound of Formula I, in unit dosage form comprising the compound either alone or in admixture with a pharmaceutically acceptable carrier appropriately selected from those known.

An effective but nontoxic quantity of the compound I is employed in treatment. The dosage regimen is selected in accordance with a variety of factors including the type, age, weight, sex, and medical condition of the mammal, the severity of symptoms of the disease being treated, the route of administration and particular compound of Formula I employed. An ordinarily skilled physician or veterinarian will readily determine and prescribe the effective amount of the compound I to prevent or arrest the progress of the disease condition. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention are ordinarily in the area of 0.1 mg/kg up to at least 1 mg/kg per dose IV, preferably to 0.1–0.3 mg/kg IV and are given as needed. When other forms of administration are employed equivalent doses are administered.

It is understood that the compositions and methods of treatment of the present invention as described above also include the pharmacologically acceptable acid addition salts of the compounds of Formula I.

The following Example further illustrates the invention.

EXAMPLE 1

2-(2-ethoxy-2-oxoethylidene)-1,2,3,4-tetrahydro-6-methyl-4-[2-(trifluoromethyl)phenyl]-3,5-pyridinedicarboxylic acid diethyl ester ($I_1$)

A solution of 3-amino-2-pentenedionic acid diethyl ester (40.3 g, 0.20 mol) and 3-oxo-2-[[2-(trifluoromethyl)phenyl]methylene]butanoic acid ethyl ester (57.6 g, 0.20 mol) in 500 ml ethanol was heated at reflux for 120 hours. The solution was concentrated to a yellow oil from which the product was isolated after several chromatographic separations, as a yellow, crystalline solid, mp 98°–99° C. Yield 6.3 g (6.7%).

Calc. C, 58.84; H, 5.58; N, 2.98. Found C, 58.71; H, 5.72; N, 2.78.

NMR (200 MHz, $CDCl_3$) d 9.95 (s, 1H), 7.62 (d, J=7.8 Hz, 1H), 4.98 (s, 1H), 4.70 (s, 1H), 4.3–3.8 (complex m, 6H), 3.24 (s, 1H), 2.52 (s, 3H), 1.24, 1.22 (overlapping triplets, J =7.1 and 7.2 Hz, 6H total), 1.04 (t, J - 71 Hz, 3H).

SCHEME I

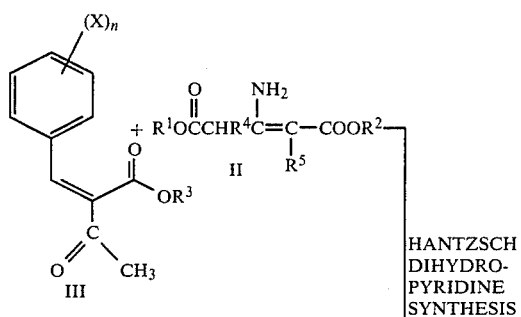

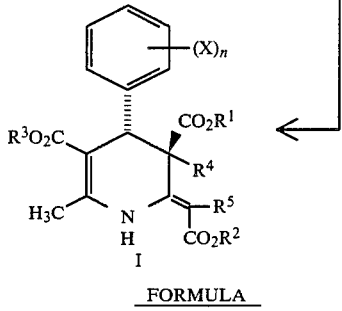

HANTZSCH DIHYDROPYRIDINE SYNTHESIS

FORMULA

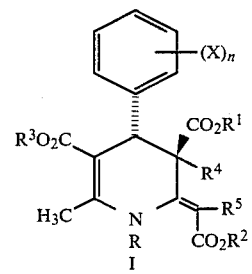

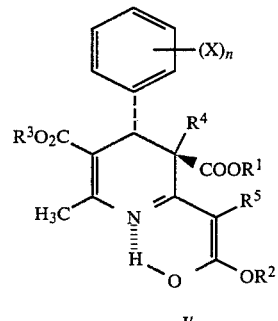

I'

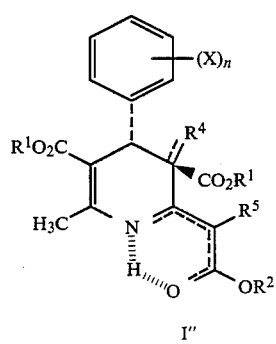

I''

We claim:

1. A compound having the formula (I)

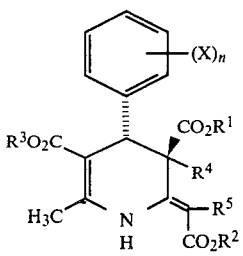

wherein $R^1$, $R^2$, and $R^3$ are independently alkyl of from one to six carbons, inclusive; $R^4$ and $R^5$ are hydrogen or alkyl of from one to six carbons, inclusive; n is an integer of one to five inclusive, X may be the same of different and is selected from one to three carbons, inclusive; $NO_2$, fluorine, chlorine, bromine, trifluoromethyl, methoxy, amino, and alkylamino of from one to six carbons, inclusive; or a pharmaceutically acceptable salt thereof.

2. A compound according to claim 1 wherein $R^1$, $R^2$, and $R^3$ are ethyl, $R^4$ and $R^5$ are hydrogen, n is 1 and X is trifluoromethyl so the specific embodiment is 2-(2-ethoxy-2-oxoethylidene)-1,2,3,4-tetrahydro-6-methyl-4-[2-(trifluoromethyl)phenyl]-3,5-pyridinecarboxylic acid diethyl ester.

3. A pharmaceutical composition for the treatment of congestive heart failure, coronary heart disease, mycardial ischemia, angine, or hypertension comprising an effective amount for use to increase myocardial contractility, and as an antimycardial ischemic, antianginal, or antihypertensive, of a compound as claimed in claim 1 together with a pharmaceutically acceptable carrier.

4. A method for treating congestive heart failure, coronary heart disease, myocardial ischemia, angina, or hypertension in a mammal suffering therefrom, which comprises administering to such mammals a compound as claimed in claim 1.

5. A method according to claim 4 wherein the mammal is a human.

* * * * *